(12) United States Patent
Yang (10) Patent No.: US 7,687,254 B2
(45) Date of Patent: Mar. 30, 2010

(54) PHENOL-FREE METHOD OF ISOLATING DNA

(75) Inventor: Jianqi Yang, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 11/776,284

(22) Filed: Jul. 11, 2007

(65) Prior Publication Data

US 2008/0033160 A1 Feb. 7, 2008

Related U.S. Application Data

(60) Provisional application No. 60/819,828, filed on Jul. 11, 2006.

(51) Int. Cl.
*C07H 21/02* (2006.01)
*C12N 1/08* (2006.01)

(52) U.S. Cl. .................. 435/270; 536/25.41; 536/25.42

(58) Field of Classification Search ........................ None
See application file for complete search history.

(56) References Cited

U.S. PATENT DOCUMENTS

| 5,234,809 A | 8/1993 | Boom et al. |
| 5,346,994 A | 9/1994 | Chomczynski |
| 5,352,777 A | 10/1994 | Jhingan |
| 5,625,053 A | 4/1997 | Kresheck et al. |
| 5,945,515 A | 8/1999 | Chomczynski |
| 6,235,501 B1 | 5/2001 | Gautsch et al. |
| 2003/0215845 A1 | 11/2003 | Bille |

OTHER PUBLICATIONS

Balansky et al., "No Effect of Treatment with Carcinogens on Cytosine Methylation of Mitochondrial DNA Isolated From Rat Organs by Phenol-Free Alkaline Extraction," Cancer Letters, 97(1), 17-23 (1995).*
Anon., SIGMA Catalog—Biochemicals and Reagents for Life Science Research, St. Louis, MO, 2000-2001, only pp. 554 and 724 supplied.*
Favre, D., "Improved Phenol-Based Method for the Isolation of DNA Fragments from Low Melting Temperature Agarose Gels," BioFeedback, 13(1), 24-26 (1992).*
Kury et al., "Determination of HER-2/neu Amplification & Expression in Tumor Tissues & Cultured Cells: Phenol-Free Method of Isolation," Oncogene, 5(9), 1403-1408 (1990).*
Pitera et al., "Modification of Standard Proteinase K/Phenol Method for Extraction of DNA from Tumor," Pathology, Research and Practice, 189(9), 882-887 (1993).*

* cited by examiner

*Primary Examiner*—Lawrence E Crane
(74) *Attorney, Agent, or Firm*—Tarolli, Sundheim, Covell & Tummino LLP (57) ABSTRACT

A phenol-free method of isolating DNA from biological material includes homogenizing a biological material with a homogenization buffer to form a homogenate. Proteins and non-DNA organic molecules are extracted from the homogenate by mixing a first extraction buffer and a second extraction buffer with the homogenate. The first extraction buffer includes chloroform and an alcohol and the second extraction buffer includes a non-ionic protein solubilizer and an alcohol. DNA is precipitated from the mixture of homogenate, first extraction buffer and second extraction buffer and the DNA is recovered by sedimentation.

20 Claims, 10 Drawing Sheets

PHENOL-FREE METHOD OF ISOLATING DNA

RELATED APPLICATION

This application claims priority from U.S. Provisional Application No. 60/819,828, filed Jul. 11, 2006, the subject matter of which is incorporated herein by reference.

TECHNICAL FIELD

The present invention relates to a method of isolating DNA, and more particularly to a phenol-free method of isolating DNA from biological material.

BACKGROUND OF THE INVENTION

The continuous advances in molecular biology, biotechnology and clinical research have resulted in an ever increasing number of uses for nucleic acids, such as DNA and RNA. For example, polymerase chain reaction (PCR) technology has dramatically expanded the use of DNA and RNA in basic research, in clinical diagnostics, such as detection of messenger RNA by reverse transcription PCR, and the use of PCR in detection of genetic defects. The increased use of DNA and RNA has created a need for fast, simple and reliable methods and reagents for isolating DNA and RNA.

Methods of isolating DNA from complex starting materials, such as while blood, blood serum, and tissue biopsies, can include lysis of biological material by detergent in the presence of protein degrading enzymes, followed by several extractions with organic solvents, e.g., phenol and/or chloroform, ethanol precipitation, and dialysis of the nucleic acids. Such methods often time-consuming, irreproducible and give DNA of variable yield and purity. Additionally, the use of phenol as a protein denaturant can be hazardous to users.

SUMMARY OF THE INVENTION

The present invention relates to a phenol-free method of isolating DNA from biological material. In the method, a biological material is homogenized with a homogenization buffer to form a homogenate. The homogenization buffer includes a chaotropic guanidine compound and 2-amino-2-(hydroxymethyl)-1-propanediol, hydrochloride (Tris HCl). Proteins and non-DNA organic molecules are then extracted from the homogenate by mixing a first extraction buffer and a second extraction buffer with the homogenate. The first extraction buffer includes chloroform and a lower alcohol, and the second extraction buffer includes a non-ionic protein solubilizer and a lower alcohol. DNA is then precipitated from the mixture of homogenate, first extraction buffer and second extraction buffer. The precipitated DNA is recovered by sedimentation.

In an aspect of the invention, the homogenization buffer can include guanidine thiocyanate, and the homogenization buffer can have a substantially neutral pH.

In another aspect of the invention, the first extraction buffer can include chloroform and iso-amyl alcohol. The second extraction buffer can have an acidic pH and can include an alcohol and octylphenolpoly(ethyleneglycolether).

In a further aspect, the biological material can be mixed with a basic lysis buffer prior to homogenizing the biological material. The basic lysis buffer can include Proteinase K and, particularly, Proteinase K, Sodium Dodecyl Sulfate (SDS), NaCl, and $CaCl_2$.

In another aspect, the DNA can be precipitated from the mixture of homogenate, first extraction buffer, and second extraction buffer by adding a lower alcohol to the mixture. The precipitated DNA can be recovered and then later mixed with a basic re-suspension solution. The re-suspension solution can include RNase A.

The present invention also relates to a phenol-free method of isolating DNA from biological material that includes homogenizing a biological material with a homogenization buffer to form a homogenate. The homogenization buffer can include guanidine thiocyanate and 2-amino-2-(hydroxymethyl)-1,-propanediol, hydrochloride (Tris HCl) (e.g., about 4 M guanidine thiocyanate and about 50 mM Tris-HCl at about pH 7.0). Proteins and non-DNA organic molecules can be extracted from the homogenate by mixing a first extraction buffer and a second extraction buffer with the homogenate. The first extraction buffer can include chloroform and iso-amyl alcohol (e.g., about 99% chloroform (v/v) and about 1% iso-amyl alcohol (v/v)). The second extraction buffer can include an acidic octylphenolpoly(ethyleneglycolether) solution and iso-amyl alcohol solution (e.g., about 1.0% octylphenolpoly(ethyleneglycolether) solution (v/v), about 0.2% iso-amyl alcohol (v/v), and about 0.3 M sodium acetate (v/v) at about pH 5.2). DNA is then precipitated from the mixture of homogenate, first extraction buffer an second extraction buffer by adding a lower alcohol to the mixture. The precipitated DNA can be recovered by sedimentation.

In another aspect, the biological material can be mixed with a basic lysis buffer prior to homogenizing the biological material. The basic lysis buffer can comprise Proteinase K, SDS, Tris-HCl, NaCl, and CaCl2.

In a further aspect, the recovered DNA can be resuspended by mixing the recovered DNA with a basic re-suspension solution. The re-suspension solution can include RNase A (e.g., about 10 mM Tris-HCl, at about pH 8.5, and about 10 µg/ml of RNase A).

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

The present invention relates to a method of isolating DNA, and more particularly to a phenol-free method of isolating DNA from biological material. The phenol-free DNA isolation method in accordance with the present invention produces a substantial yield of high quality, readily soluble DNA in less time than conventional DNA isolation procedures.

The method of the present invention provides a highly effective, simple means of isolating DNA from biological material, such as cells, tissues and biological fluids. Advantageously, DNA isolation in accordance with the method of the present invention can be achieved at room temperature, without the use of a column (i.e., column free) and without the use of toxic agents, such as phenol (i.e., phenol-free). The DNA isolation method can also provide a high yield DNA from biological materials known to have high intrinsic nuclease activity, such as the spleen, liver, and kidney (e.g., about 12 µg DNA/mg spleen tissue).

DNA isolation in accordance with the method of the present invention is substantially faster than existing methods for the isolation of DNA and allows a larger number of samples to be processed. For example, DNA can be isolated from biological material in less than about 30 minutes (e.g., less than about 15 minutes) utilizing the method of the present invention.

Additionally, DNA isolated using the method of the present invention has a high quality, which allows it to be used in research, such as with PCR and/or Southern blotting. For instance, DNA isolated by the method of the present invention is readily soluble and has a size that allows it to be readily compatible with down stream reactions.

Figure 1:
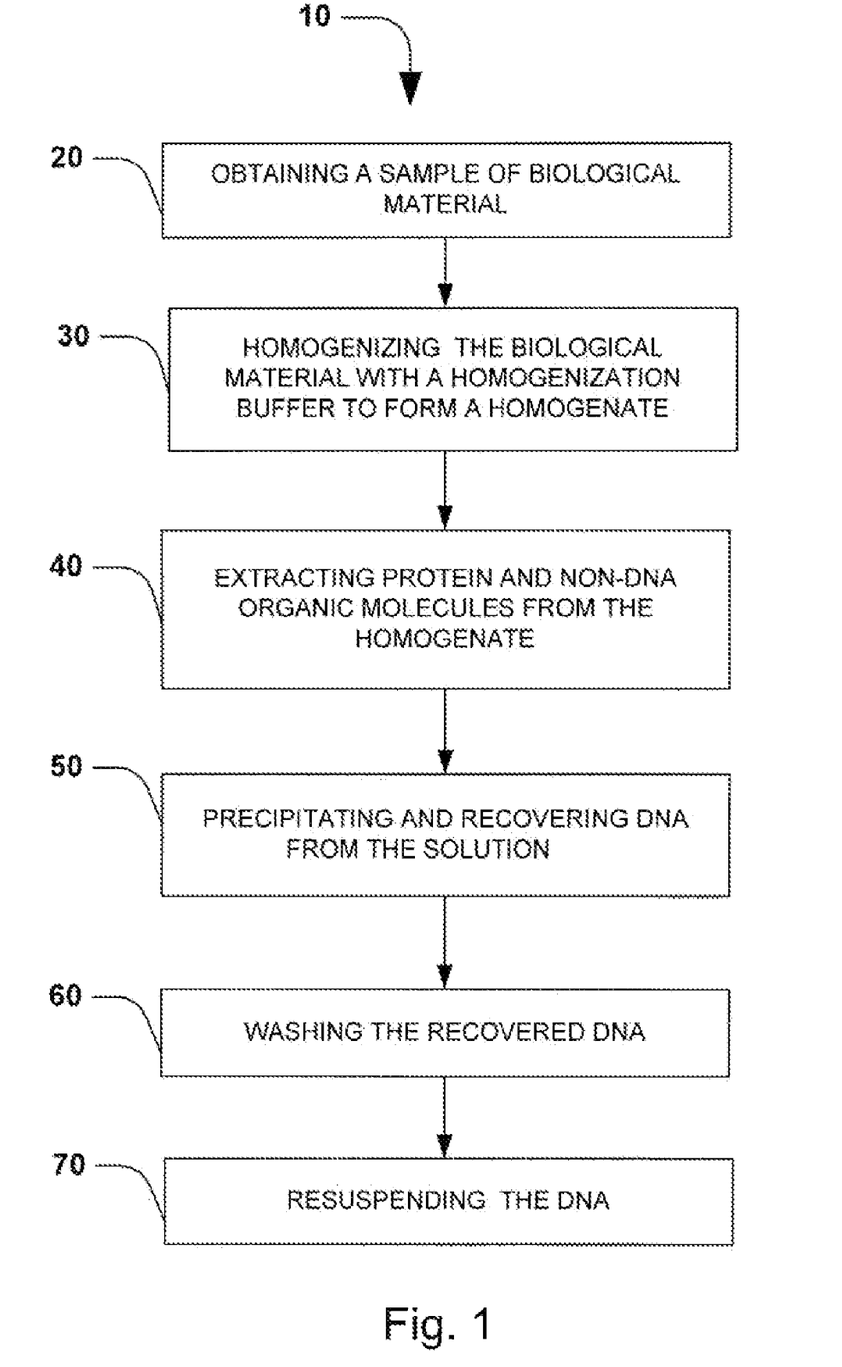
FIG. 1 is a flow diagram illustrating a method in accordance with one aspect of the invention.

FIG. 1 is a flow diagram illustrating a phenol-free method 10 of isolating DNA from a sample of biological material in accordance with one aspect of the present invention. In the method 10, at 20 a sample of biological material is obtained. The biological material can include animal tissue that is obtained by, for example, biopsy from any one or combination of organs and/or tissue structures including the brain, heart, kidney(s), liver, intestines, adipose tissue, lung(s), ovary(ies), pancreas, muscle, cartilage, skin, spleen, stomach, tail and testis. The biological material can also be obtained from a cultured cell colony, e.g., a primary cell line or continuous cell line propagated in vitro.

At 30, an amount of the obtained biological material is homogenized with a homogenization buffer to form a homogenate. The homogenate is formed by mixing the biological material with the homogenization buffer. The homogenization buffer can include a substantially neutral aqueous solution of a chaotropic guanidine compound and 2-amino-2-(hydroxymethyl)-1-propanediol, hydrochloride (Tris-HCl). The chaotropic guanidine compound can include any chaotropic guanidine compound, such as a guanidine salt, that is capable of altering the secondary, tertiary, and/or quaternary structure of the proteins and nucleic acids and inhibits the activity of nucleic acid degradation enzymes in the biological material. Examples of such chaotropic guanidine compounds include guanidine thiocyanate and guanidine chloride. By way of example, the homogenization buffer can include about 3.5 M to about 4.5 M (e.g., about 4 M) guanidine thiocyanate and about 30 mM to about 70 mM (e.g., about 50 mM) Tris-HCl at about pH 7.0.

The amount of biological material contacted and homogenized with the quantity of homogenization buffer depends on the particular source of the biological material and the quantity of homogenization buffer utilized. The following table lists examples of particular biological tissues and corresponding amounts that are combined with 0.24 ml of homogenization buffer to form the homogenization solution.

TABLE

| Samples | Recommended amount | Maximal amount | Approximate yield (µg/mg sample) |
|---|---|---|---|
| Bacteria pellet (wet) | 15 mg | 30 mg | ~2.0 |
| Yeast pellet (wet) | 30 mg | 60 mg | ~1.5 |
| Whole blood | ~0.1 ml* | 0.15 ml* | 35 ug/ml* |
|  | ~0.01 ml** | 0.02 ml** | 2.2 mg/ml** |
| Cell pellet (wet) | 10 mg | 20 mg | ~6.0 |
| Brain | 10 mg | 30 mg | ~1.0 |
| Brown adipose tissue | 20 mg | 60 mg | ~0.2 |
| White adipose tissue | 60 mg | 120 mg | ~0.05 |
| Heart | 10 mg | 30 mg | ~0.5 |
| Kidney | 10 mg | 30 mg | ~2.0 |
| Large intestine | 10 mg | 30 mg | ~3.0 |
| Liver | 10 mg | 30 mg | ~2.5 |
| Lung | 5 mg | 15 mg | ~3.0 |
| Ovary | 5 mg | 15 mg | ~4.0 |
| Pancreas | 10 mg | 30 mg | ~2.5 |
| Skeletal muscle | 30 mg | 50 mg | ~0.05 |
| Skin | 10 mg | 30 mg | 3.0 |
| Small intestine villi | 10 mg | 30 mg | ~2.5 |
| Small intestine wall | 10 mg | 30 mg | ~4.0 |
| Spleen | 5 mg | 8 mg | ~10.0 |
| Stomach | 10 mg | 30 mg | ~2.0 |
| Testis | 5 mg | 20 mg | ~3.5 |
| Tail (in length) | 3 mm | 6 mm | ~10 µg/mm tail‡ |
| Plant leaves | 30 mg | 50 mg | ~0.5 |

*Species with non-nucleated erythrocytes
**Species with nucleated erythrocytes
‡Yield of DNA from tails vary with age of animal.

The biological material can be contacted with the quantity of homogenization buffer by, for example, placing the sample of biological material and the homogenization buffer in a 2-ml homogenization tube containing the homogenization buffer. The sample may then be homogenized at about 20 rpm to yield a homogenization solution. For example, the sample may be homogenized by applying about 10 to about 15 strokes at about 20 to about 40 seconds per stroke until homogenization solution is uniform and there is no visible material remaining. Where multiple biological material samples are used, each of the samples may be homogenized and prepared as described above.

Alternatively, where the biological material sample includes cultured cells, the cells may be collected from 1 well of a 6-well plate for example, by pouring out the culture medium, scraping the cells into 1×PBS, transferring the cells to a 1.5-ml tube, and then centrifuging the tube for about 1 minute, at about 12,000 rpm. After centrifugation, the supernatant may be removed and about 0.24 ml of the homogenization buffer added to the tube. The cell pellet may then be re-suspended, e.g., by pipetting several times until no visible cell pellet remains. It should be appreciated by one skilled in the art that the cell pellet may be frozen after centrifugation and then subsequently re-suspended as desired.

At 40, after homogenizing the biological material sample, protein and non-DNA organic molecules are extracted from the homogenate. By non-DNA organic molecules, it is meant organic molecules in the biological material other than or not including nucleic acids, such as DNA. The organic molecules can be extracted from the homogenate by mixing the homogenate with a first extraction buffer for organic molecules. The first extraction buffer for organic molecules can include a non-aqueous solution that is capable of extracting the organic molecules from the homogenate. In an aspect of the invention, the non-aqueous solution can include chloroform and a lower alcohol (e.g. a branched or straight chain alcohol with less than about 6 carbon atoms). The chloroform can be provided in the first extraction buffer at greater than about 90%, about 95%, or about 98% by volume (e.g., about 99% by volume). The lower alcohol can include, for example, iso-amyl alcohol. The iso-amyl alcohol can be provided in the first extraction buffer at less than about 10%, 5%, or 2% by volume (e.g., about 1% by volume). The quantity of first extraction buffer contacted with the homogenate can be, for example, about 0.2 ml.

The second extraction buffer can be used to extract protein and polypeptides from the homogenate. The second extraction buffer for protein can include an acidic solution which includes a non-ionic protein solubilizer and a lower alcohol. The non-ionic protein solubilizer can include, for example, an aqueous solution of octylphenolpoly(ethyleneglycolether), such as Nonidet P40 (NP-40), which is commercially available from Roche Diagnostics GmbH (Mannheim, Germany). In one aspect of the invention, the acidic solution can include about 0.50% to about 2.0% (e.g., about 1.0%) NP-40 lysis buffer (v/v), about 0.1% to about 0.5% (e.g. about 0.2%) iso-amyl alcohol (v/v), and about 0.1 M to about 0.5 M (e.g., about 0.3 M) sodium acetate at about pH 5.2. The quantity of the second extraction buffer added to the homogenate can be, for example, about 0.8 ml.

The homogenization solution, the first extraction buffer, and the second extraction buffer can be mixed by, for example, overtaxing the homogenization solution and the first extraction buffer and the second extraction buffer for about 5 seconds. The mixed homogenate solution, first extraction buffer, and second extraction buffer can then be centrifuged for about 4 minutes at about 12,000 rpm to form a first supernatant and a first pellet.

At 50, the DNA in the supernatant can be precipitated and recovered by mixing a quantity of the first supernatant with a quantity of a lower alcohol (e.g., methanol, ethanol, or iso-propanol) to precipitate the DNA. The precipitated sedimented DNA can then be, by for example centrifuging the mixture to form a first pellet. By way of example, about 0.63 ml of iso-propanol can be provided in a 1.5-ml tube. About 0.88 ml of the first supernatant can then be added to the tube. The tube may be mixed, e.g., by shaking, and then centrifuged for about 2 minutes at about, 12,000 rpm to form the second supernatant and second pellet of sedimented DNA. The second supernatant can be carefully removed from each tube so as to not dislodge the remaining second pellet.

At 60, the second pellet of precipitated DNA can be removed from the supernatant, washed with a quantity of lower alcohol (e.g., methanol, ethanol, or iso-propanol), and then centrifuged. For example, the pellet can be washed with about 1.0 ml of about 70% ethanol and again centrifuged for about 4 minutes at about 12,000 rpm to form a third supernatant and third pellet of DNA. After centrifugation, the third supernatant may be removed and the remaining pellet dried about 15 minutes using about 37° C. warm air. Alternatively, the third pellet of DNA may be dried overnight at room temperature.

Optionally, at 70 the pelletized DNA can be resuspended in solution by dissolving the pellet in, a re-suspension solution (e.g., about 150 µl of re-suspension solution). The re-suspension solution can comprise, for example, about 10 mM Tris-HCl, at about pH 8.5, and about 10 µg/ml of RNase A. The pellet may be re-suspended by several pulses of vortexing, for example, and the re-suspended DNA may be used as desired. Alternatively, the re-suspended DNA may be stored at about 4° C. until needed.

Figure 2:
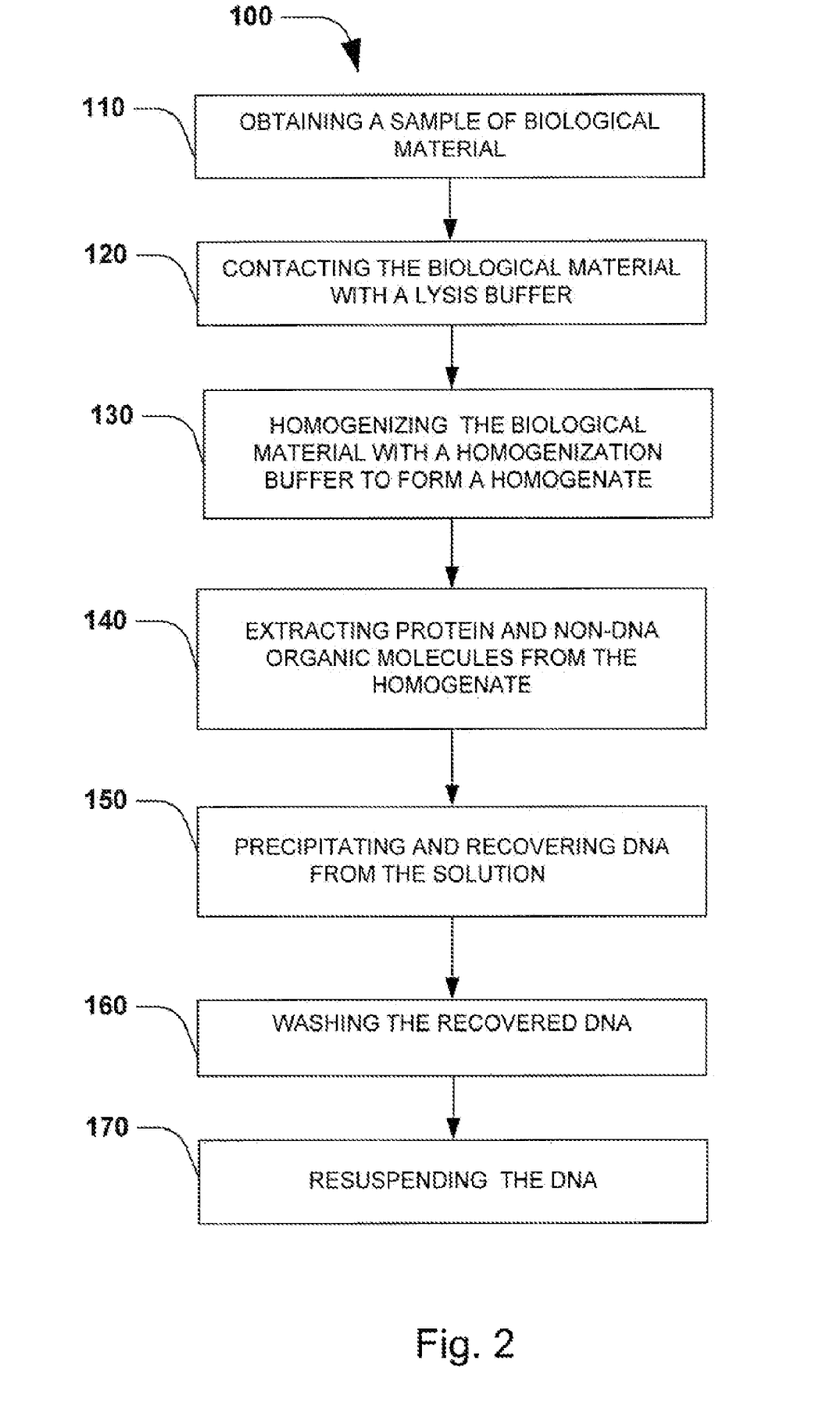
FIG. 2 is a flow diagram illustrating a method in accordance with another aspect of the invention.

FIG. 2 is a flow diagram illustrating a phenol-free method 100 of isolating DNA from biological material in accordance with another aspect of the invention. The DNA isolation method in accordance with this aspect can be advantageously used to isolate DNA from cartilage based animal tissue.

In the method 100, at 110 a sample of a biological material is obtained. The biological material sample can include animal tissue that is obtained by, for example, biopsy from cartilaginous tissue. The cartilaginous tissue can include a tail or tail piece from a rat or mouse. For example, a cartilage sample having a length of about 3 mm may be harvested in an appropriate manner and then placed in a 1.5-ml tube.

At 120, a sample of biological material is contacted with a quantity of a lysis buffer to dissolve or breakdown the tissue. The lysis buffer may comprise, for example, about 100 mM Tris-HCl at about pH 8.0, about 0.5% Sodium Dodecyl Sulfate (SDS) (w/v), about 100 mM NaCl, and about 2 mM $CaCl_2$. The lysis buffer may be supplemented with an amount of Proteinase K sufficient to bring the final concentration of Proteinase K in the lysis buffer to about 200 µ/ml. The quantity of lysis buffer contacted with the biological material depends on the amount of biological material used. For example, about 0.2 ml of a lysis buffer can be combined with about 10 mg to about 20 mg of mouse tail (e.g., about 3 mm in length) to form a lysis solution.

The tube containing the aqueous lysis solution and the sample may then be incubated at about 56° C. for about 1 hour while being occasionally shaken. The sample may be incubated until most of the tail tissue, excluding the tailbone, is dissolved.

At 130, the lysis solution containing the sample is contacted with a quantity of homogenization buffer and then homogenized to form a homogenate. The homogenization buffer can include a substantially neutral aqueous solution of a chaotropic guanidine compound and 2amino-2-(hydroxymethyl)-1-propanediol, hydrochloride (Tris-HCl). By way of example, the homogenization buffer can include about 3.5 M to about 4.5 M (e.g., about 4 M) guanidine thiocyanate and about 30 mM to about 70 mM (e.g., about 50 mM) Tris-HCl at about pH 7.0. The quantity of homogenization buffer added to lysis solution can be, for example, about 0.4 ml. The homogenate may then be vortexed for about 5 seconds.

At 140, after homogenizing the biological material sample, protein and non-DNA organic molecules are extracted from the homogenate. The organic molecules can be extracted from the homogenate by mixing the homogenate with a first extraction buffer for organic molecules. The first extraction buffer for organic molecules can include a non-aqueous solution that is capable of extracting the organic molecules from the homogenate. In an aspect of the invention, the non-aqueous solution can include chloroform and at lower alcohol (e.g., a branched or straight chain alcohol with less than about 6 carbon atoms). The chloroform can be provided in the first extraction buffer at greater than about 90%, about 95%, or about 98% by volume (e.g., about 99% by volume). The lower alcohol can include for example, iso-amyl alcohol. The iso-amyl alcohol can be provided in the first extraction buffer at less than about 10%, 5%, or 2% by volume (about 1% by volume). The quantity of first extraction buffer contacted with the homogenate can be, for example, about 0.2 ml.

The second extraction buffer can be used to extract protein and polypeptides from the homogenate. The second extraction buffer for protein can include an acidic solution which includes a non-ionic protein solubilizer and a lower alcohol. The non-ionic protein solubilizer can include, for example, an aqueous solution of octylphenolpoly(ethyleneglycolether), such as Nonidet P40 (NP-40), which is commercially available from Roche Diagnostics GmbH (Mannheim, Germany). In one aspect of the invention, the acid solution can include about 0.5% to about 2.0% (e.g., about 1.0%) NP-40 lysis buffer (v/v), about 0.1% to about 0.5% (e.g. about 0.2%) iso-amyl alcohol (v/v), and about 0.1 M to about 0.5 M (e.g., about 0.3 M) sodium acetate at about pH 5.2. The quantity of the second extraction buffer added to the homogenate can be, for example, about 0.45 ml.

The homogenization solution, the first extraction buffer, and the second extraction buffer can be mixed by, for example, vortexing the homogenate and the first extraction buffer and the second extraction buffer for about 5 seconds. The mixed homogenate, first extraction buffer, and second extraction buffer call then centrifuged for about 4 minutes at about 12,000 rpm to form a first supernatant and a first pellet.

At 150, the DNA in the first supernatant can be precipitated and recovered by mixing a quantity of the first supernatant with a quantity of a lower alcohol (e.g., methanol, ethanol, or iso-propanol) to precipitate the DNA. The precipitated DNA can then be sedimented, by for example centrifuging the mixture to form a first pellet. By way of example, about 0.63 ml of iso-propanol can be provided in a 1.5-ml tube. About 0.88 ml of the first supernatant can then be added to the tube. The tube may be mixed, e.g., by shaking, and then centrifuged for about 2 minutes at about 12,000 rpm to form the second supernatant and second pellet of sedimented DNA. The second supernatant can be carefully removed from each tube so as to not dislodge the remaining second pellet.

At 160, the second pellet of precipitated DNA can be removed from the supernatant and washed with a quantity of lower alcohol (e.g., methanol, ethanol, or iso-propanol), and then centrifuged. For example, the pellet can be washed with about 1.0 ml of about 70% ethanol and again centrifuged for about 4 minutes at about 12,000 rpm to form a third supernatant and third pellet of DNA. After centrifugation, the third supernatant may be removed and the remaining pellet dried for about 15 minutes using about 37° C. warm air. Alternatively, the third pellet of DNA may be dried overnight at room temperature.

Optionally, at 170, the pelletized DNA can be resuspended in solution by dissolving the pellet in, for example, about 150 μl of a re-suspension solution. The re-suspension solution can comprise, for example, about 10 mM Tris-HCl, at about pH 8.5, and about 1.0 μg/ml of RNase A. The pellet may be re-suspended by several pulses of vortexing, for example, and the re-suspended DNA may be used as desired. Alternatively, the re-suspended DNA may be stored at about 4° C. until needed.

The following examples are included to demonstrate various aspects of the invention. Those of skill in the art should, in light of the present disclosure, appreciate that many changes can be made in the specific aspects which are disclosed and still obtain a like or similar result without departing from the spirit and scope of the invention.

EXAMPLE 1

Quality and Size of Isolated Genomic DNA

Figure 3:
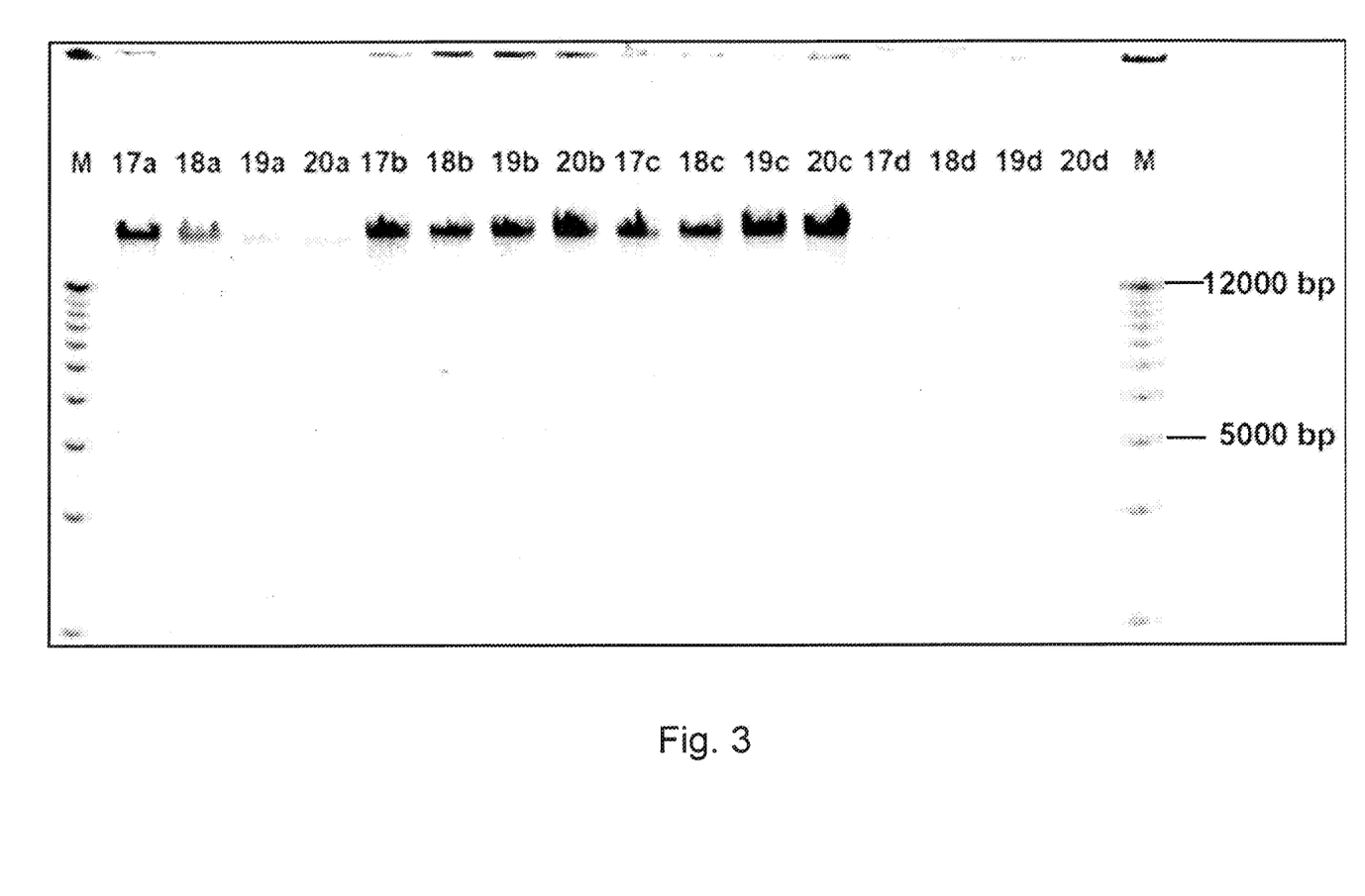
FIG. 3 is an agarose gel showing DNA isolated from mouse liver tissue in accordance with the present invention.

Various isolation and solutions in accordance with the present invention were tested, and the quality of resultant DNA was analyzed using a 0.8% agarose gel (FIG. 3). FIG. 3 is an agarose gel showing DNA isolated from mouse liver tissue in accordance with the present invention. The DNA in each lane accounts for 5 μl of a total 300 μl reaction. The DNA ladder is a 1 Kb plus from Invirogen. FIG. 3 indicates that for DNA isolated by the method of the present invention there is no degradation and DNA size is large.

EXAMPLE 2

Digestions with Restriction Enzyme

Figure 4A:
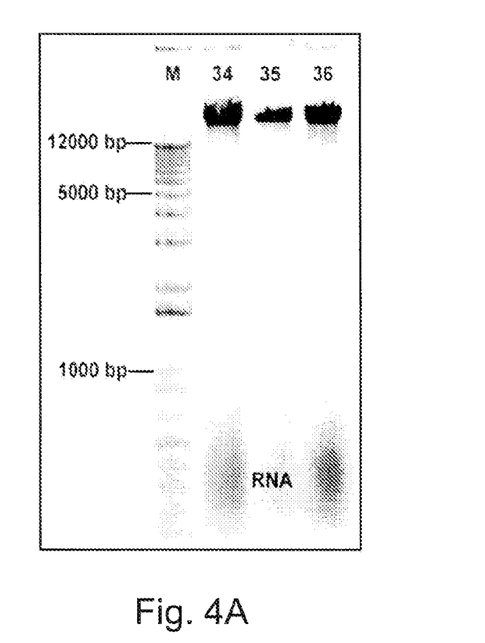
FIGS. 4A-C show agarose gels before genomic DNA digestion with EcoRI (FIG. 4A), after genomic DNA digestion with EcoRI (FIG. 4B), and after digestion with other restriction enzymes (FIG. 4C).
Figure 4B:
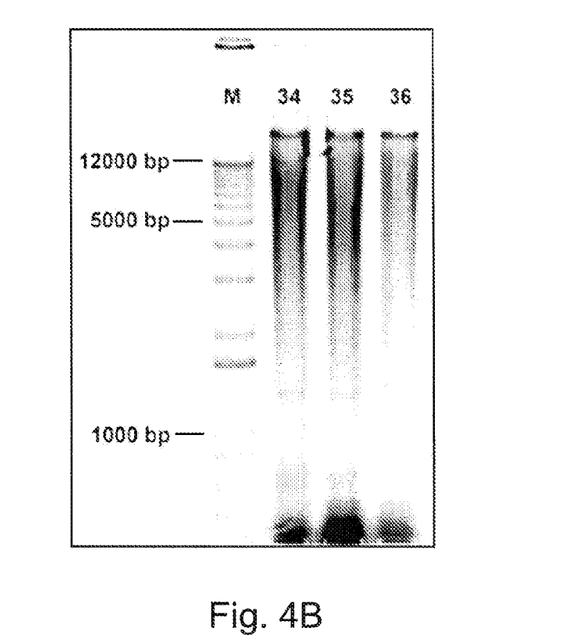
Figure 4C:
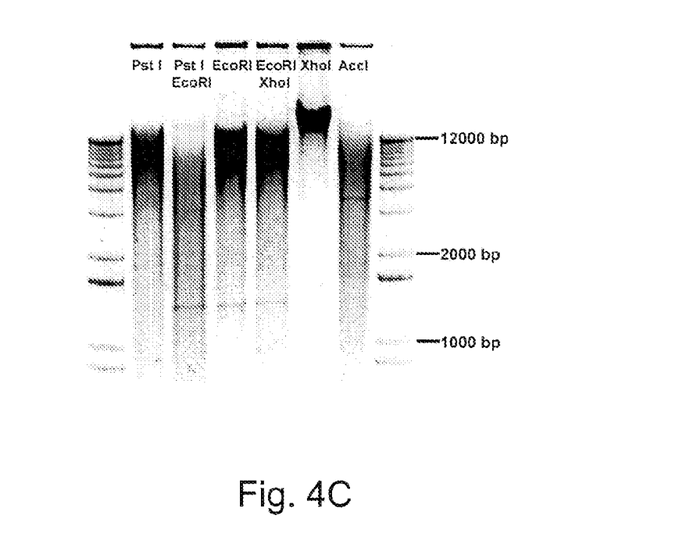

Genomic DNA, isolated from mouse liver in accordance with the method of present invention, was digested with restriction enzyme. The isolated DNA was dried completely using 37° C. warm air, and dissolved in 300 μl of 10 mM Tris-HCl at pH 8.5 (no RNase) for 20 minutes without (A). FIG. 4A shows an agarose gel before genomic DNA digestion with EcoRI. FIG. 4B shows an agarose gel after genomic DNA digestion with EcoRI. FIG. 4C shows an agarose gel after genomic DNA digestion with a single or combination or restriction enzymes. DNA ladder is 1 Kb Plus from Invitrogen.

EXAMPLE 3

Isolation of Genomic DNA

Figure 5A:
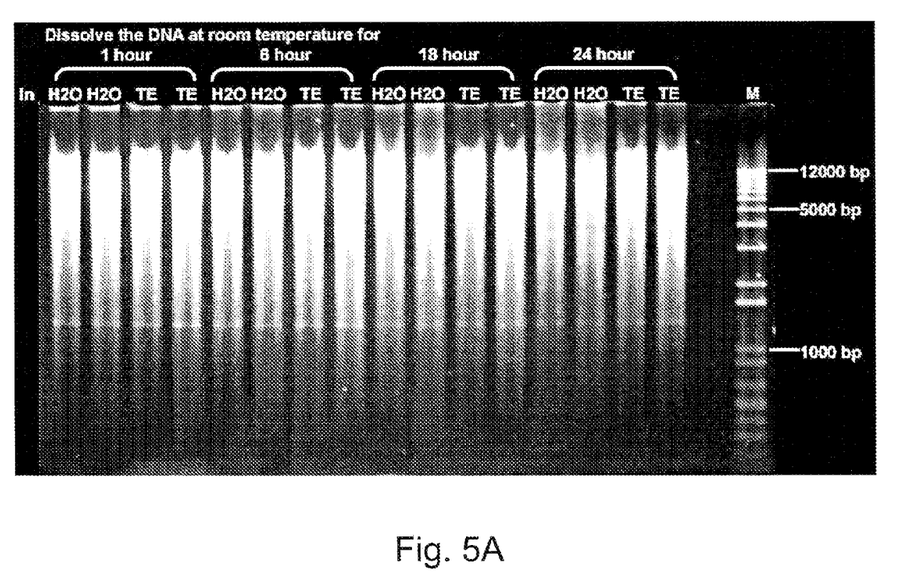
FIGS. 5A-B show the solubility (FIG. 5A) and long-term stability (FIG. 5B) of isolated genomic DNA.
Figure 5B:
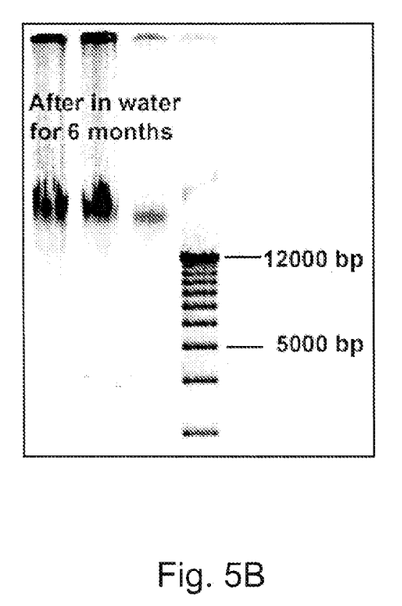

FIG. 5A is an agarose gel showing genomic DNA, isolated from mouse liver using the method in accordance with the present invention, was dried completely using 37° C. warm air, dissolved in 300 μl of water or TE for 1, 6, 18, 24 hs. The resultant DNA, solution was then digested with EcoRI at 37° C. for 2 hs. FIG. 5B shows that DNA was dissolved in water and kept at 4° C. for 6 months. There is no detectable degradation. DNA ladder is 1 Kb Plus from Invitrogen.

EXAMPLE 4

Isolation of Genomic DNA form Various Tissues

Figure 6A:
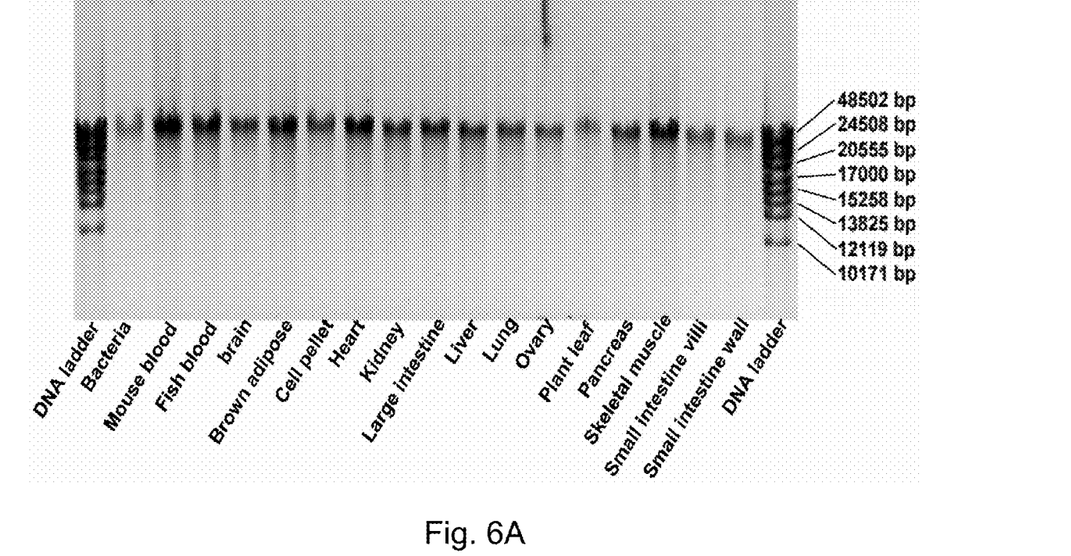
FIGS. 6A-B are agarose gels showing genomic DNA isolated from various biological specimens.
Figure 6B:
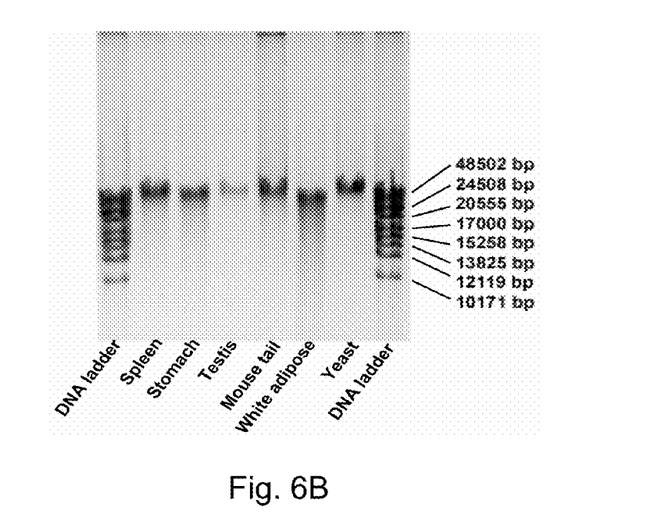

FIGS. 6A and FIG. 6B show agarose gels loaded with genomic from various biological specimens, including various mouse tissues mouse blood, fish blood, bacteria, cell pellet, yeast, and plant. The length of isolated genomic DNA is around 40 kb. DNA ladder is from Fermentas Life Science.

EXAMPLE 5

EcoRI Digestion of Genomic DNA form Various Tissues

Figure 7A:
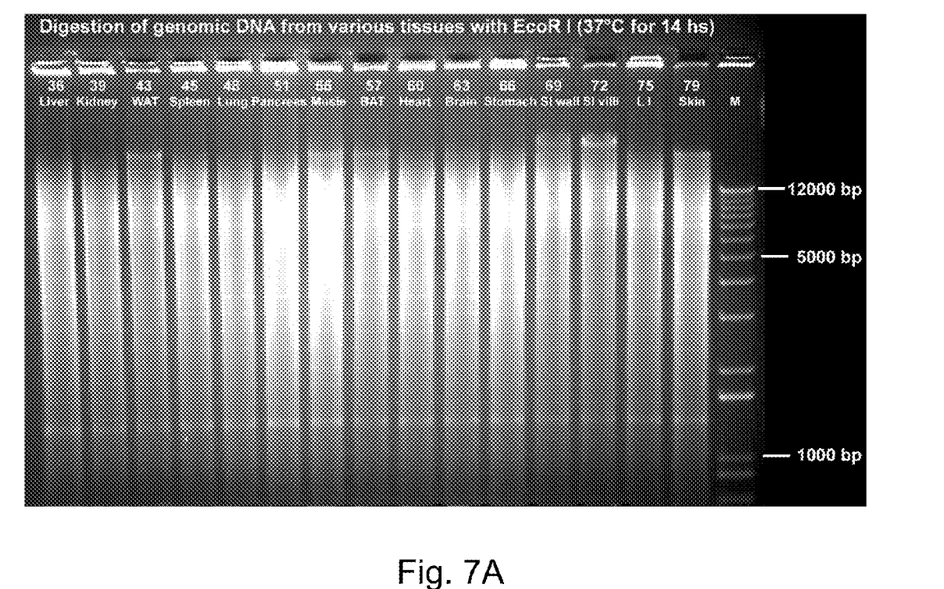
FIGS. 7A-B show two agarose gels loaded with genomic DNA from various tissues digested with EcoRI.
Figure 7B:
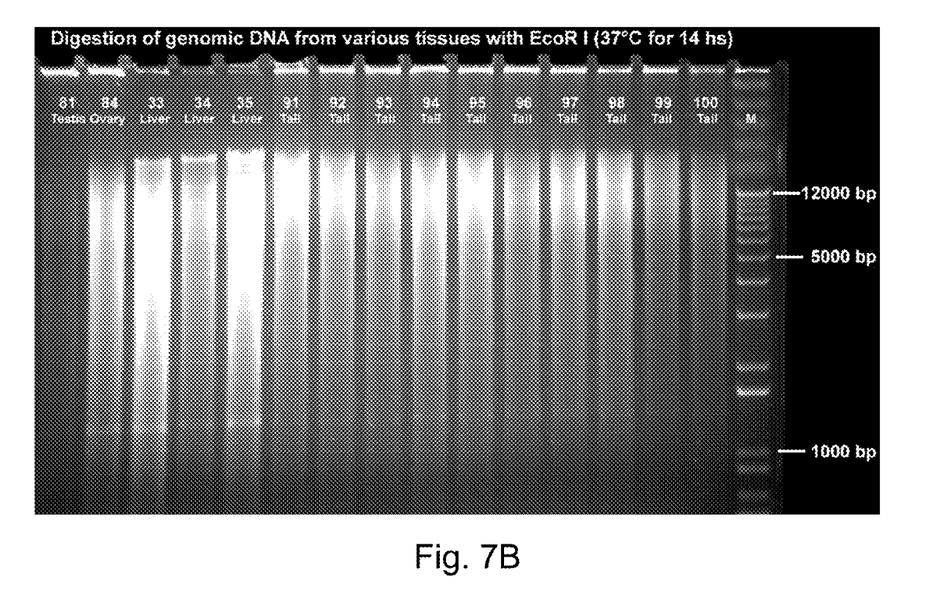

FIGS. 7A and 7B show two agarose gels loaded with genomic DNA (about 8 μg). The Genomic was digested with EcoRI (100 units) at 37° C. for 14 hours.

EXAMPLE 6

Southern Blot

Figure 8:
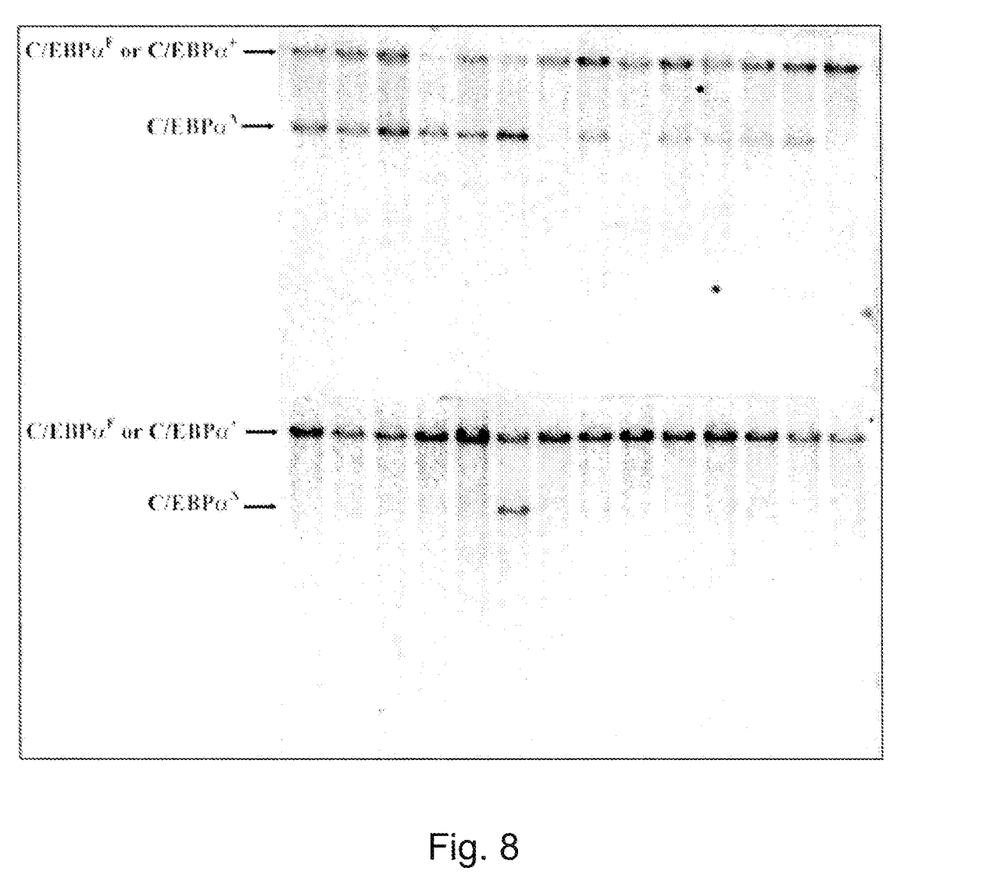
FIG. 8 is a Southern blot showing genomic DNA digested EcoRI and probed for C/EBPα alleles.

FIG. 8 is a Southern blot showing genomic DNA digested with EcoRI and probed for C/EBPα alleles.

EXAMPLE 7

Figure 9:
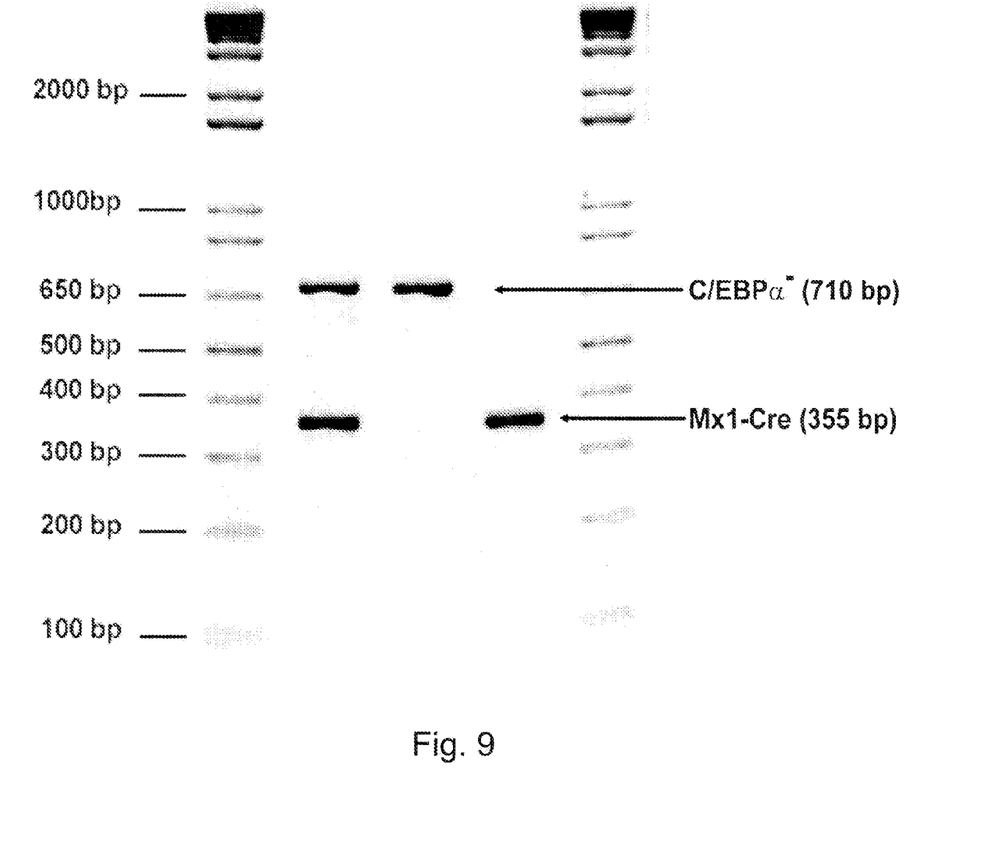
FIG. 9 is a PCR result using genomic DNA isolated from mouse tails.

FIG. 9 is a PCR result using genomic DNA isolated from mouse tails. Genomic DNA isolated from mouse tails was used to perform PCR to genotype two transgenic of C/EBPα⁻ and Mx1-Cre.

EXAMPLE 8

Figure 10:
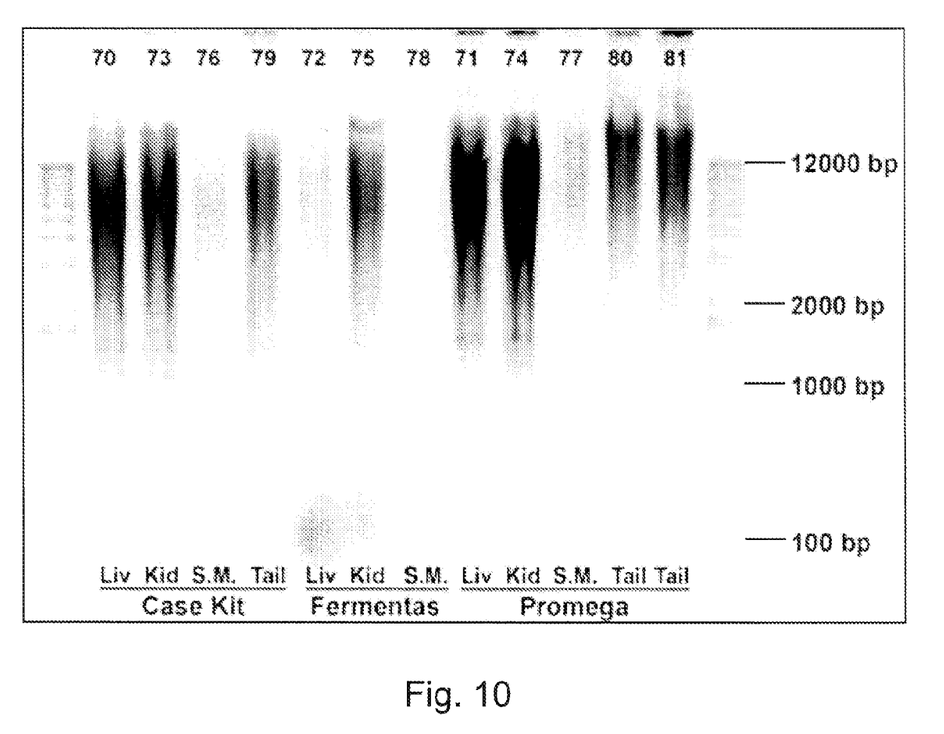
FIG. 10 shows an agarose gel comparing the DNA isolation method of the present invention to prior art DNA isolation methods.

FIG. 10 shows an agarose gel comparing the method of the present invention to prior art methods (kits from Fermentas Life Sciences and Promega Corporation). After digestion with EcoR I, DNA was analyzed in 0.8% agarose gel. Kid, Kidney; Liv, Liver; S. M., Skeletal Muscle.

From the above description of the invention those skilled in the art will perceive improvements, changes and modifications. For instance, the present invention may also be used to isolate RNA. Such improvements, changes and modifications within the skill of the art are intended to be covered by the appended claims.

I claim:

1. A phenol-free method of isolating DNA from biological material, comprising:
   homogenizing a biological material with a homogenization buffer to form a homogenate, the homogenization buffer comprising a chaotropic guanidine compound and 2-amino-2-(hydroxymethyl)-1-propanediol, hydrochloride (Tris HCl);
   extracting proteins and non-DNA organic molecules from the homogenate by mixing a first extraction buffer and a second extraction buffer with the homogenate, the first extraction buffer comprising chloroform and an alcohol and the second extraction buffer comprising a non-ionic protein solubilizer and an alcohol; and
   precipitating DNA from the mixture of homogenate, first extraction buffer and second extraction buffer and recovering the DNA by sedimentation.

2. The method of claim 1, wherein the homogenization buffer comprises guanidine thiocyanate.

3. The method of claim 2, wherein the homogenization buffer has a pH of about 7.

4. The method of claim 1, wherein the first extraction buffer comprises chloroform and iso-amyl alcohol.

5. The method of claim 1, wherein the second extraction buffer comprises an alcohol and octylphenolpoly(ethyleneglycolether).

6. The method of claim 1, further comprising mixing the biological material with a lysis buffer prior to homogenizing the biological material.

7. The method of claim 6, the lysis buffer comprising Proteinase K.

8. The method of claim 6, the lysis buffer comprising Proteinase K, Sodium Dodecyl Sulfate (SDS), Tris-HCl, NaCl, and $CaCl_2$.

9. The method of claim 1, the DNA being precipitated from the mixture of homogenate, first extraction buffer, and second extraction buffer by adding a lower alcohol to the mixture.

10. The method of claim 1 further comprising the step of contacting the recovered DNA with a basic re-suspension solution, the re-suspension solution comprising RNase A.

11. A phenol-free method of isolating DNA from biological material, comprising:
    homogenizing a biological material with a homogenization buffer to form a homogenate, the homogenization buffer comprising a guanidine thiocyanate and 2-amino-2-(hydroxymethyl)-1-propanediol, hydrochloride (Tris HCl);
    extracting proteins and non-DNA organic molecules from the homogenate by mixing a first extraction buffer and a second extraction buffer with the homogenate, the first extraction buffer comprising chloroform and iso-amyl alcohol and the second extraction buffer comprising octylphenolpoly(ethyleneglycolether); and
    precipitating DNA from the mixture of homogenate, first extraction buffer and second extraction buffer by adding a lower alcohol to the mixture and recovering the DNA by sedimentation.

12. The method of claim 11, wherein the homogenization buffer has a pH of about 7.

13. The method of claim 11, wherein the second extraction buffer has a pH of about 5.2.

14. The method of claim 11, further comprising mixing the biological material with a lysis buffer prior to homogenizing the biological material.

15. The method of claim 14, the lysis buffer comprising Proteinase K, SDS, Tris-HCl, NaCl, and $CaCl_2$.

16. The method of claim 11, further comprising the step of contacting the recovered DNA with a basic re-suspension solution, the re-suspension solution comprising RNase A.

17. A phenol-free method of isolating DNA from biological material comprising the steps of:
    homogenizing a biological material with a homogenization buffer to form a homogenate, the homogenization buffer comprising about 4 M guanidine thiocyanate and about 50 mM Tris-HCl at about pH 7.0;
    extracting proteins and non-DNA organic molecules from the homogenate by mixing a first extraction buffer and a second extraction buffer with the homogenate, the first extraction buffer comprising about 99% chloroform (v/v) and about 1% iso-amyl alcohol (v/v), the second extraction buffer comprising about 1.0% octylphenolpoly(ethyleneglycolether) solution (v/v), about 0.2% iso-amyl alcohol (v/v), and about 0.3 M sodium acetate (v/v) at about pH 5.2; and
    precipitating DNA from the mixture of homogenate, first extraction buffer and second extraction buffer by adding a lower alcohol to the mixture and recovering the DNA by sedimentation.

18. The method of claim 17 further comprising the step of mixing the biological material with a lysis buffer prior to homogenization, the lysis buffer comprising about 100 mM Tris-HCl at about pH 8.0, about 0.5% SDS (w/v), about 100 mM NaCl, and about 2 mM $CaCl_2$.

19. The method of claim 18, wherein the lysis buffer further comprising an amount of Proteinase K effective to bring the final concentration of Proteinase K in the lysis buffer to about 200 µg/ml.

20. The method of claim 17, further including the step of contacting the recovered DNA with a re-suspension solution, the re-suspension solution comprising about 10 mM Tris-HCl, at about pH 8.5, and about 10 µg/ml of RNase A.

\* \* \* \* \*